United States Patent [19]

Brown et al.

[11] Patent Number: 5,184,624
[45] Date of Patent: Feb. 9, 1993

[54] ELECTRICAL IMPEDANCE TOMOGRAPHY

[75] Inventors: Brian H. Brown; David C. Barber, both of Sheffield, England

[73] Assignee: The University of Sheffield, Sheffield, England

[21] Appl. No.: 850,242

[22] Filed: Mar. 11, 1992

Related U.S. Application Data

[63] Continuation of Ser. No. 623,759, Dec. 12, 1990, abandoned.

[30] Foreign Application Priority Data

Apr. 15, 1988 [GB] United Kingdom ................ 8808969

[51] Int. Cl.$^5$ ............................................. A61B 5/05
[52] U.S. Cl. ................................................. 128/734
[58] Field of Search ..................................... 128/734

[56] References Cited

U.S. PATENT DOCUMENTS 4,486,835 12/1984 Bai et al. ............................. 128/734

OTHER PUBLICATIONS

Henderson et al., "An Impedance Camera for Spatially Specific Measurements of the Thorax" IEEE Transactions on Biomedical Engineering, vol. BME25 No. 3 May 1978, pp. 250-254.

Price, "Electrical Impedance Computed Tomography, (ICT): A New CT Imaging Technique" IEEE Transactions on Nuclear Science, vol. NS-26 No. 2 Apr. 1979 pp. 2736-2739.

Murphy et al, "Algorithms for Electrode Positioning and Configuration in Impedance Imaging", IEEE Eighth Annual Conference of the Engineering in Medicine and Biology Society, Nov. 7-10 1986 vol. 2 pp. 1181-1182.

Primary Examiner—Ruth S. Smith
Attorney, Agent, or Firm—Trexler, Bushnell, Giangiorgi & Blackstone, Ltd.

[57] ABSTRACT

A method of determining the external shape of a body comprises placing a plurality of electrodes adjacent the surface at spaced intervals around the body, causing currents to flow in the body by applying an electrical potential between pairs of electrodes in turn, measuring potentials between other pairs of electrodes, relating the measured potentials to the distances between the corresponding points of current introduction and of potential measurement, and determining electrode positions consistent with these distances, which electrode positions define the external shape of the body.

5 Claims, 2 Drawing Sheets

ELECTRICAL IMPEDANCE TOMOGRAPHY

This application is a continuation of application Ser. No. 07/623,759, filed Dec. 12, 1990 now abandoned.

BACKGROUND OF THE INVENTION

This invention relates to tomography of the type described in GB-2119520B in which tomographic images of a body are constructed by placing a plurality of surface electrodes at spaced intervals on the body, causing currents to flow in the body, and measuring the potentials between pairs of electrodes, calculating the potential in each case on the assumption that the body consists of one uniform medium, plotting the isopotentials corresponding to the calculated results to create a uniform image of the body, obtaining the ratio between the measured potential and the calculated potential in each case, and modifying the image in accordance with the respective ratios by increasing the impedance along an isopotential in proportion to a ratio greater than unity or decreasing the impedance in proportion to a ratio less than unity.

The calculations of potentials and the obtaining of ratios have been carried out using a computer, and the plotting of the isopotentials have been carried out by a visual display unit (VDU) and/or a print-out run off the computer.

An additional method is provided for indicating a change of state in the body in GB-2160323B, and this method includes the step of determining ratios between initial and subsequent measured actual potentials between electrodes.

The voltage measured between a pair of electrodes connected to a body surface when a current is applied between a second pair of electrodes applied to the body surface depends on (a) the relative positions of the electrodes on the surface; (b) the shape of the body surface and (c) the internal impedance distribution within the body. (a) is the dominant factor followed by (b) and then (c). However the use of a calculated or measured reference set allows the contributions from (a) and (b) to be largely eliminated from the image reconstruction calculation; the differences in the sets of measurements between the 'reference' set and the 'data' set are dependent almost solely on the changes in internal impedance.

Both methods are described in U.S. Pat. No. 4,617,939 and both methods assume that the cross-sectional shape of a body is circular and thus produce circular images, which may not be satisfactory if the true cross-sectional shape is far from circular, as is frequently the case.

SUMMARY OF THE INVENTION

An object of the present invention is the determination of the external shape of a body preparatory to obtaining tomographic images of it.

Another object is to construct a tomographic image that accurately depicts the internal structure of the body.

According to the present invention, a method of determining the external shape of a body comprises placing a plurality of electrodes adjacent the surface at spaced intervals around the body, causing currents to flow in the body by applying an electrical potential between pairs of electrodes in turn, measuring potentials between other pairs of electrodes, using the measured potentials to calculate estimated distances between the corresponding points of current introduction and of potential measurement, and determining electrode positions consistent with these distances, which electrode positions define the external shape of the body.

The external shape of the body can be plotted, e.g., on a VDU and or as a print-out, by means of a computer, on the assumption that the body consists of one uniform medium and plotting the image of electrode positions corresponding to the measured values.

DETAILED DESCRIPTION OF THE INVENTION

Figure 1:
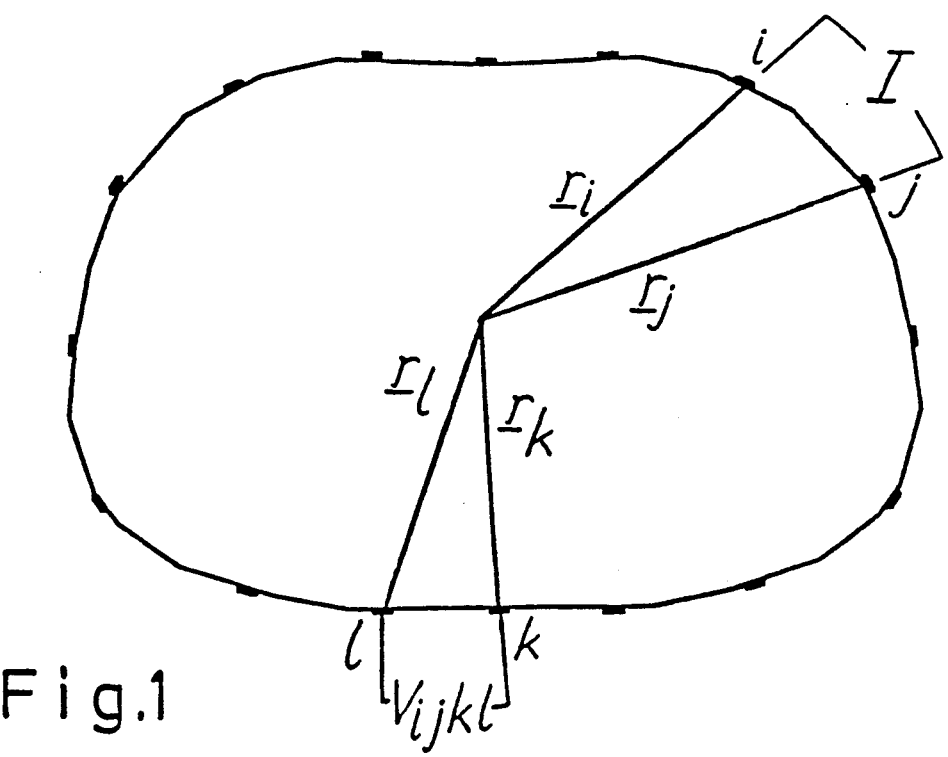
FIGS. 1-3 are diagrammatic representations of tomographic measurements according to a method provided in the present invention.

The method of determining the external shape of a body will now be described with reference to the diagrammatic FIGS. 1 to 3 of the accompanying drawings.

The following describes how a single set of measurements ('data') can be used to calculate the shape of the boundary and generate a computed set of reference measurements.

THEORY

If N electrodes defining a plane are connected to the body surface then a measurement set consists of $N(N-3)/2$ independent measurements if drive electrodes are adjacent to each other or $N(N-4)/2$ otherwise. The voltages measured between a pair of electrodes (k,z) when a current I is applied between a second pair of electrodes (i,j) is given by (FIG. 1)

$$V_{ijkz} = I \cdot F_{(ri,rj,rk,rz,b(r),c(r))}$$

where ri,rj,rk,rz are the positions of the electrodes, b (r) is the function representing the boundary and c(r) is the internal impedance distribution. Since the $V_{ijkz}$ are only weakly dependent on c(r) this can be replaced by c, a uniform impedance throughout the object. Similarly since the dependence of $V_{ijkz}$ on b(r) is weaker than the dependence on electrode position, these can be combined into a single function F' of the electrode position. In the absence of a boundary this function can be obtained from simple geometric considerations alone. In the presence of a boundary this function will deviate from this ideal form in a way that may be modelled empirically. In summary $$V_{ijkz} = IcF'_{(ri,rj,rk,rz)} \tag{1}$$

Given the set of measured V and a model of the function F' the position vectors r of the N electrodes may be computed and hence the boundary determined. In the absence of an exact model of F' the fact that there are at least $N(N-4)/2$ independent measurements and only 2N electrode coordinates are required and since 2N is significantly less than $N(N-4)/2$, an accurate result ensues since substantially more measurements are provided than the number of co-ordinates that are needed to provide accuracy. For a similar reason these computed electrode positions are not sensitive to the internal impedance distribution; data from non-uniform and uniform internal impedance distributions will generate almost the same electrode positions. By inserting the electrode positions back into Equation 1 values of $V_{ijkz}$ corresponding to a 'reference' distribution may be generated and used to calculate images of absolute impedance in conjunction with the measured 'data' set.

If the voltages are always measured between adjacent electrodes, current is also always applied between adjacent electrodes, the spacing between adjacent electrodes is constant and this spacing is small compared to the dimensions of the body then empirically the function $F'$ may be represented by $$F(d) = \frac{1}{d_{ik}{}^n}$$

Figure 2:
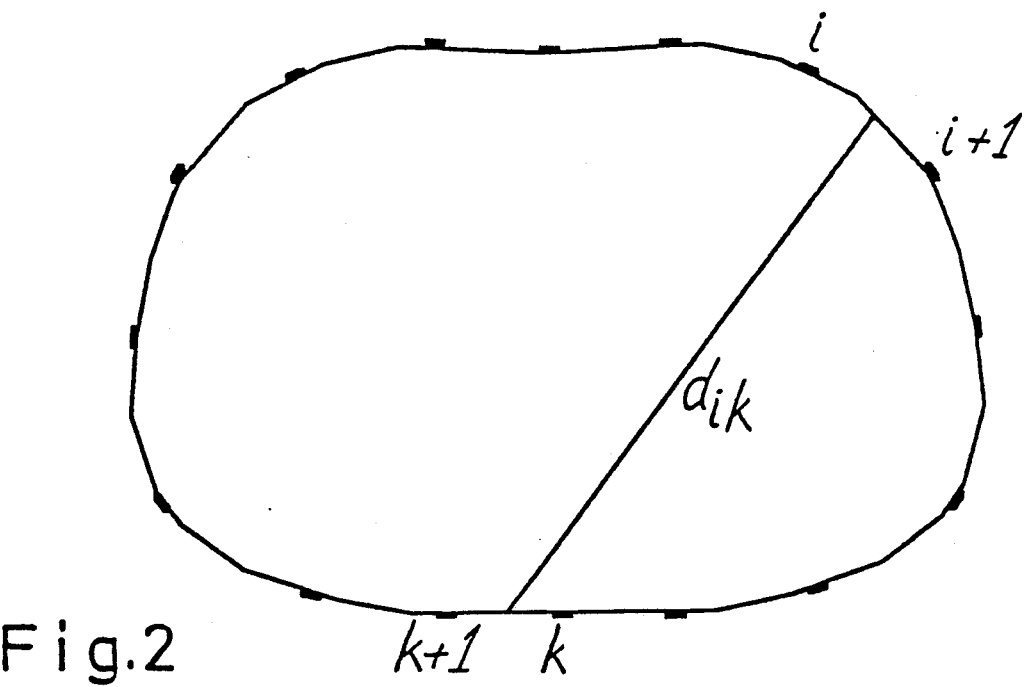
Figure 3:
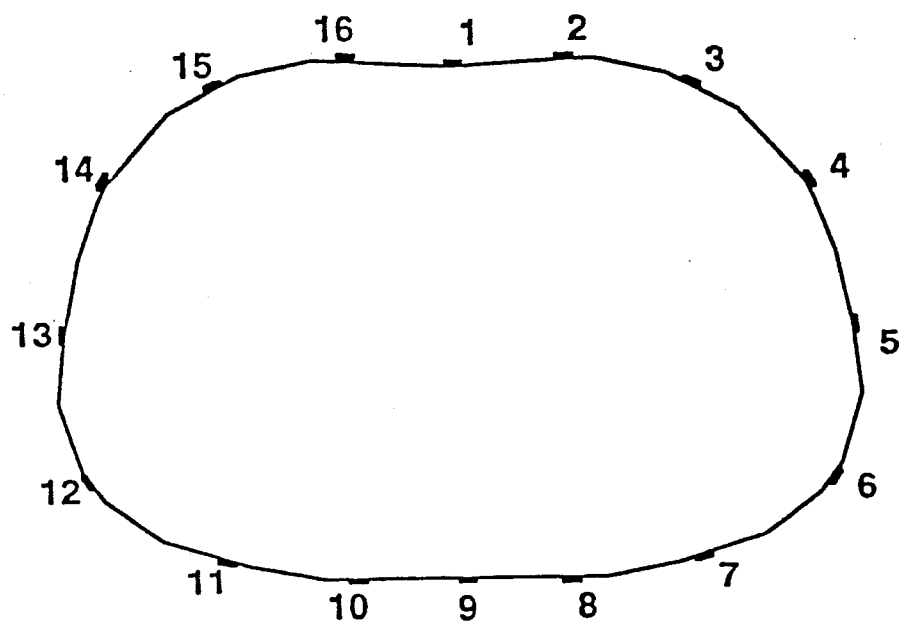

$v_{i,i+1,k,k+1}$ by $V_{ik}$ $$V_{ik} = \frac{C}{d_{ik}{}^n}$$

where $d_{ik}$ is the distance between the midpoint between the electrodes i and i+1 and the midpoint between electrodes k and k+1 (FIG. 2). A value of n=3.7 has proved effective.

The starting point for determining the boundary shape is a circular boundary with equally spaced electrodes. Two pairs of electrodes are taken (typically those placed at the ends of the maximum diameter of the body) and the coordinates of these electrode pairs fixed. The distance between them is chosen, (this fixes the scale of the boundary) and the constant C in $$V_{ik} = \frac{C}{d_{ik}^{3.7}} \quad (2)$$

is computed from this distance and the measured value of $V_{ik}$. Changing the scale of this reference d simply changes the value of the constant C. For the remaining pairs of 'drive' and 'receive' electrode pairs the distances between them are calculated from $$d_{ik} = \left(\frac{C}{V_{ik}}\right)^{\frac{1}{3.7}}$$

Consider a 'drive' pair initially situated on the circular boundary and a 'receive' pair also on the boundary. The value of d is computed and this distance is measured out along the line joining the 'drive' and 'receive' pairs from the 'drive' pair. The point at the end of this distance is now taken to be a new estimate of the position of the 'receive' pair. This process is repeated for all combinations of 'drive' and 'receive' electrode pairs. For each electrode pair there are N−3 position co-ordinate pairs calculated. These are averaged to give mean co-ordinate values. The co-ordinates of all the "received" electrode pairs now define a new boundary, no longer circular. The process of co-ordinate estimation is now repeated until no further change in the co-ordinate estimates occurs. Estimation of the electrode co-ordinate (and boundary shape) is now complete (FIG. 3). Faster convergence may be obtained if a starting boundary shape (e.g. an ellipse) closer to that of the required boundary shape than a circle is chosen. Once the boundary shape has been defined an appropriate form of the function $F'$ in equation 1 may be determined from the measured values of $V_{ijkz}$ and the calculated electrode co-ordinate and used to calculate reference values.

More accurate estimates of boundary shape may be achieved by (a) a more complex version of $F'$ than that given in Equation 2, such as $$V_{ik} = \frac{c\left(2 - \frac{d_{ik}{}^2}{4}\right)^n}{(d_{ik})^m}$$

where n=1.0 and m=2.6, or (b) choice of a simple form for $F'$ but restriction of its use to a pre-selected subset of drive and receive pairs.

Figure 4:
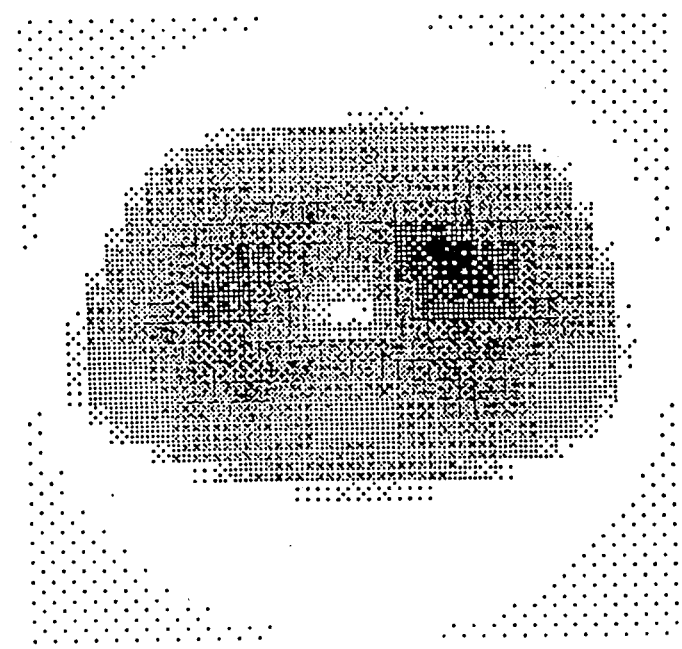
FIG. 4 is a representative tomographic image generated by computer using a method according to the invention.

A tomographic image that accurately depicts the internal structure of the body can be constructed by calculating the potential between pairs of electrodes on the assumption that the body consists of one uniform medium, plotting the isopotentials corresponding to the calculated results to form an image, obtaining the ratio between the measured potential and the calculated potential in each case, and modifying the image in accordance with the respective ratios by increasing the impedance along an isopotential in proportion to a ratio greater than unity or decreasing the impedance in proportion to a ratio less than unity, as described in GB-2119520B. A typical print-out image is shown in FIG. 4 of the accompanying drawings.

Again, as described in GB-2160323B and U.S. Pat. No. 4,617,939, the method can be adapted for indicating a change of state in the body by determining ratios between initial and subsequent measured actual potentials between electrodes.

We claim:

1. A method of determining the external shape of a body comprising placing a plurality of surface electrodes at spaced intervals around the body, causing currents of known value to flow in the body by applying an electrical current between pairs of electrodes in sequence, in each case measuring potentials between other pairs of electrodes, using the measured potentials to calculate estimated distances between the corresponding points of current introduction and of potential measurement, and determining estimated electrode positions consistent with these distances, which estimated electrode positions define the external shape of the body.

2. A method as in claim 1, wherein the process of electrode position estimation is repeated until no further change in the position estimates occurs.

3. A method as in claim 1 or claim 2, wherein the external shape of the body is displayed by means of a computer, on the basis of the estimated electrode positions.

4. A method of constructing a tomographic image that accurately depicts the fixed internal structure of a body comprising the method of determining the external shape of the body as in claim 1 and then calculating the potential between pairs of electrodes with the body deemed to consist of one uniform medium, plotting the isopotentials corresponding to the calculated results to form an image, obtaining the ratio between the measured potential and the calculated potential in each case, and modifying the image in accordance with the respective ratios by increasing the impedance along an isopotential in proportion to a ratio greater than unity or decreasing the impedance in proportion to a ratio less than unity.

5. A method of constructing a tomographic image according to claim 4, further comprising: determining ratios between initial and subsequent measured potentials between electrodes respectively before and after a change in the internal structure of the body.

* * * * *